United States Patent [19]

Sasaki et al.

[11] Patent Number: 4,590,175

[45] Date of Patent: May 20, 1986

[54] PROCESS FOR THE PRODUCTION OF ANTIMONY-CONTAINING METAL OXIDE CATALYSTS

[75] Inventors: Yutaka Sasaki; Hiroshi Utsumi; Kunio Mori; Hiroshi Yamamoto; Yoshimi Nakamura; Kiyoshi Moriya; Akimitsu Morii, all of Kanagawa; Mikio Noda, Tokyo; Miki Kunitani, Kanagawa, all of Japan

[73] Assignee: Nitto Chemical Industry Co., Ltd., Tokyo, Japan

[21] Appl. No.: 655,612

[22] Filed: Sep. 28, 1984

[30] Foreign Application Priority Data

Sep. 28, 1983 [JP] Japan ................................ 58-178314

[51] Int. Cl.$^4$ ............................................ B01J 21/08
[52] U.S. Cl. ...................................... 502/249; 502/237
[58] Field of Search ................................ 502/249, 237

[56] References Cited

U.S. PATENT DOCUMENTS

| Re. 30,545 | 3/1981 | Khoobiar | 502/249 |
|---|---|---|---|
| 3,197,419 | 7/1965 | Callahan et al. | 502/249 |
| 3,198,750 | 8/1965 | Callahan et al. | 502/249 |
| 3,397,153 | 8/1968 | Sippel | 502/249 |
| 3,445,521 | 5/1969 | Callahan et al. | 502/249 |
| 3,657,155 | 4/1972 | Yoshino et al. | 502/249 |
| 3,662,016 | 5/1972 | Furuoya et al. | 502/249 |
| 3,686,138 | 8/1972 | Yoshino et al. | 502/249 |
| 4,374,759 | 2/1983 | Khoobiar | 502/249 |
| 4,504,599 | 3/1985 | Sasaki | 502/249 |

*Primary Examiner*—John Doll
*Assistant Examiner*—Lance Johnson
*Attorney, Agent, or Firm*—Sughrue, Mion, Zinn, Macpeak & Seas

[57] ABSTRACT

A process for the production of antimony-containing metal oxide catalysts, comprising preparing a slurry containing as essential components an antimony component, a polyvalent metal compound, and silica sol, heating and drying the slurry to form a solid product, and then calcining the solid product, wherein the antimony component is a mixture of (A) at least one of antimonic acid, polyantimonic acid and the salts thereof and (B) antimony trioxide, and is prepared by mixing (A) and (B) in such a manner that the antimony provided by the (B) constitutes from 0.1 to 70 atomic % of the total amount of antimony and further in an aqueous slurry state. These antimony-containing metal oxide catalysts have superior activity and physical properties, and further reproducibility in the preparation thereof. Thus they are useful for production of aldehydes and acids through oxidation, nitriles through ammoxidation, and dienes, unsaturated aldehydes and unsaturated acids through oxidative dehydrogenation.

23 Claims, 12 Drawing Figures

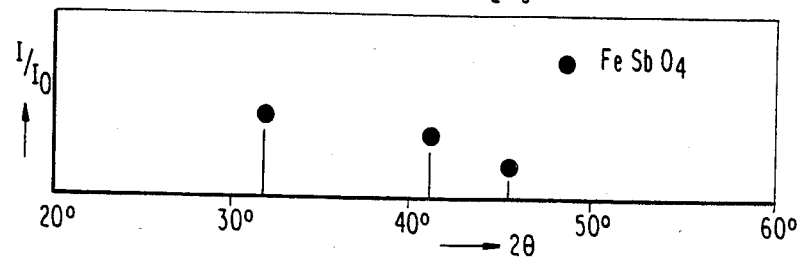
FIG.1A (EXAMPLE 1, THE SLURRY WITH NO $Sb_2O_3$ ADDED THERETO)
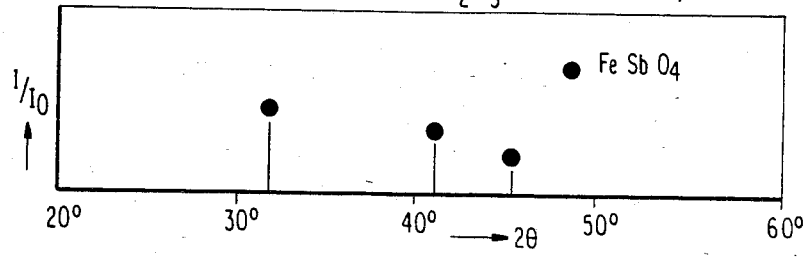
FIG.1B (EXAMPLE 1, THE SLURRY WITH $Sb_2O_3$ ADDED THERETO)
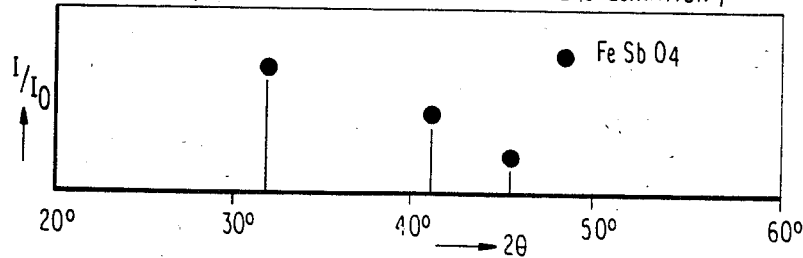
FIG.1C (EXAMPLE 1, CATALYST PRECURSOR BEFORE FINAL CALCINATION)
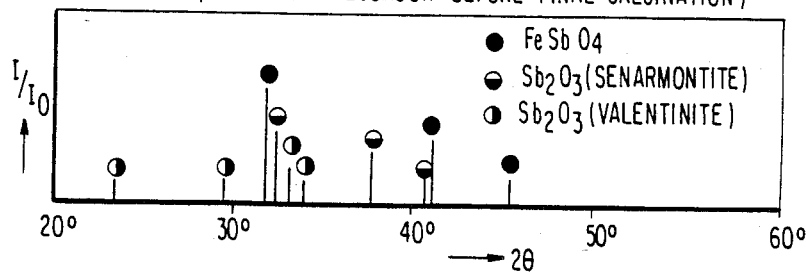
FIG.1D (COMP. EX. 2, CATALYST PRECURSOR BEFORE FINAL CALCINATION)

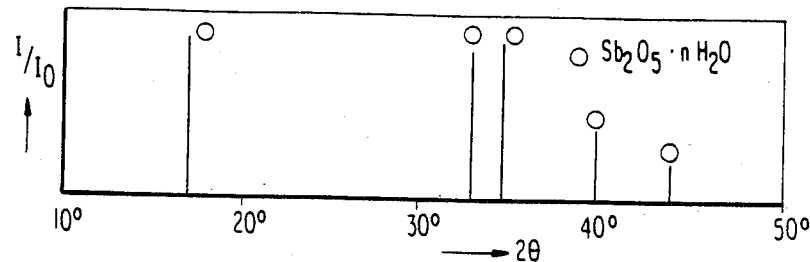
FIG. 2A (ANTIMONIC ACID SLURRY)
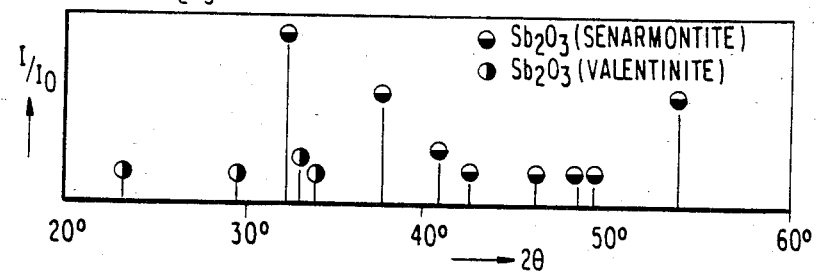
FIG. 2B ($Sb_2O_3$)
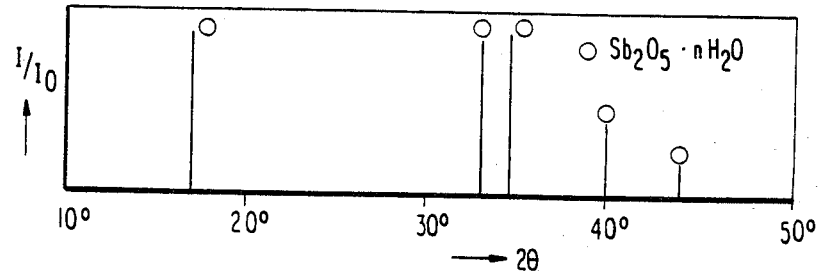
FIG. 2C (ADDITION OF $Sb_2O_3$ INTO ANTIMONIC ACID SLURRY)

PROCESS FOR THE PRODUCTION OF ANTIMONY-CONTAINING METAL OXIDE CATALYSTS

FIELD OF THE INVENTION

The present invention relates to a process for the production of antimony-containing metal oxide catalysts. More particularly it is concerned with a process for producing antimony-containing metal oxide catalysts of high activity which are useful for reactions such as oxidation, oxidative dehydrogeneation, and ammoxidation of organic compounds.

BACKGROUND OF THE INVENTION

It is known that antimony-containing metal oxide catalysts, specifically those comprising the oxides of antimony and at least one metal selected from the group consisting of iron, cobalt, nickel, tin, uranium, chromium, copper, manganese, titanium, and cerium are useful for the production of aldehydes and acids through oxidation of organic compounds, the production of dienes, unsaturated aldehydes and unsaturated acids through oxidative dehydrogenation, and the production of nitriles through ammoxidation. Japanese Patent Publication No. 19111/64, for example, discloses a useful catalyst for production of acrylonitrile through ammoxidation of propylene, comprising the oxides of antimony and iron, cobalt or nickel. It is described in U.S. Pat. No. 3,197,419 that a catalyst comprising the oxides of antimony and iron is useful for oxidation and ammoxidation of olefins. In addition, a catalyst comprising the oxides of antimony and tin is described in Japanese Patent Publication No. 14075/62 (corresponding to U.S. Pat. No. 3,152,170); a catalyst comprising the oxides of antimony and uranium, in Japanese Patent Publication No. 24367/65 (corresponding to U.S. Pat. No. 3,308,151); a catalyst comprising the oxides of antimony and manganese in U.S. Pat. No. 3,200,081; and a catalyst comprising the oxide of antimony and a metal selected from Cr, Co, Cu, Ni, or Ti in U.S. Pat. No. 3,340,291.

Attempts have been made to improve the above catalysts through addition of other components. For example, catalyst compositions comprising the oxides of antimony and iron, the oxides of antimony and tin, or the oxides of antimony and uranium, and the oxides of at least one element selected from the group consisting of vanadium, molybdenum and tungsten, and tellurium are proposed as multiply promoted antimony-polyvalent metal oxide catalysts in Japanese Patent Publication Nos. 2804/71 (corresponding to U.S. Pat. No. 3,668,147), 40985/72, and 19764/72.

These antimony-containing metal oxide catalysts, however, have various problems; for example, poor reproducibility in preparation of the catalysts, difficulty in preparing catalysts having high strength, and low operation efficiency in preparation of the catalyst. To overcome these problems, several improvements in preparation of the catalysts have been proposed, including those as described in Japanese Patent Publication Nos. 22476/67 (corresponding to U.S. Pat. No. 3,341,471), 3456/71, 3457/71, 18722/72 (corresponding to U.S. Pat. No. 3,657,155), and 18723/72 (corresponding to U.S. Pat. No. 3,686,138).

These methods, however, are not satisfactory from an industrial standpoint; that is, problems still remain to be solved in connection with, for example, satisfactory improvements in both activity and physical properties, and reproducibility. One of the problems is that in preparation of catalysts for use in a fluidized-bed reactor, as shown in Comparative Example 6 as described hereinafter, the density of the catalyst particles is increased. This adversely influences the state of the fluidized-bed catalyst during the reaction and in turn, the reaction. Furthermore, these catalysts give unsatisfactory yields of the desired product and other properties.

SUMMARY OF THE INVENTION

The present invention relates to improvements in the production of antimony-containing metal oxide catalysts. It has been found that if specific amounts of (A) at least one of antimonic acid, polyantimonic acid and the salts thereof, and (B) antimony trioxide are mixed in an aqueous slurry and are used as an antimony starting material in preparing the catalyst, the ultimate catalyst has satisfactory catalyst activity as well as physical properties, and further preparation reproducibility, whereas if the antimony components (A) and (B) are mixed in a dry state and are used as the antimony starting material in preparing the catalyst, the ultimate catalyst is not improved to a satisfactory extent.

The present invention provides a process for producing an antimony-containing metal oxide catalyst which comprises (1) preparing an aqueous slurry containing as essential components an antimony component, a polyvalent metal compound, and silica sol, (2) heating and drying the slurry to form a solid product, and (3) then calcining the solid product, where in the process the antimony component employed in step (1) is a mixture of (A) at least one of antimonic acid, polyantimonic acid and the salts thereof and (B) antimony trioxide, and the process comprises mixing components (A) and (B) in such a manner that the amount of antimony provided by the antimony trioxide is from 0.1 to 70 atomic % of the total amount of antimony present in an aqueous slurry just before drying, and the mixing is carried out in an aqueous slurry state.

BRIEF DESCRIPTION OF THE DRAWINGS

FIGS. 1A to 1C are X-ray diffraction patterns (CoK$\alpha$) of samples collected during the course of preparation of the catalyst of Example 1.

FIG. 1D is an X-ray diffraction pattern (CoK$\alpha$) of a sample collected during the course of preparation of the catalyst of Comparative Example 2.

It can be seen from FIG. 1B that in accordance with the process of the present invention (Example 1), crystalline antimony trioxide undergoes a reaction in the aqueous catalyst slurry and is converted into an amorphous form. On the other hand, in Comparative Example 2, as can be seen from FIG. 1D, antimony trioxide remains unchanged.

FIGS. 2A to 2C are X-ray diffraction patterns, illustrating the reaction between antimonic acid or polyantimonic acid and antimony trioxide.

FIGS. 3A to 3E are electronmicrographs of samples, where

Figure 3A:
Figure 3B:
Figure 3C:
Figure 3D:
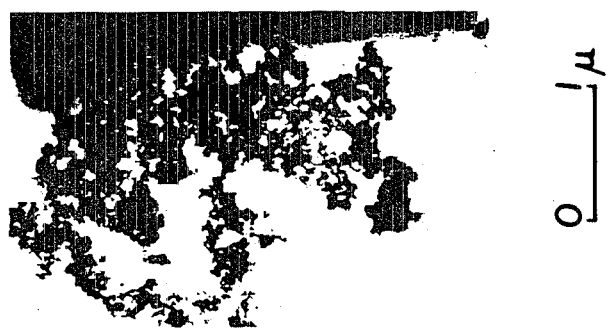
Figure 3E:

FIG. 3A is an electronmicrograph of the slurry with no antimony trioxide added thereto as prepared in Example 1 (corresponding to the sample of FIG. 1A);

FIG. 3B is an electronmicrograph of the slurry with antimony trioxide added thereto as prepared in Example 1 (corresponding to the sample of FIG. 1B);

FIG. 3C is an electronmicrograph of antimony trioxide used (corresponding to the sample of FIG. 2B);

FIG. 3D is an electronmicrograph of the antimonic acid slurry (corresponding to the sample of FIG. 2-1); and FIG. 3E is an electronmicrograph of a mixture of the antimonic acid slurry and antimony trioxide which is undergoing reaction.

The X-ray diffraction pattern of the slurry of FIG. 3E in which the reaction has been completed is shown in FIG. 2C.

In the process of the present invention, antimony trioxide crystals having a size of the order of microns (as shown in FIG. 3C) are pulverized into particles several tens of millimicrons in size on reacting with antimonic acid or polyantimonic acid. This pulverization process is clearly shown in FIGS. 3A, 3B, 3D, and 3E.

DETAILED DESCRIPTION OF THE INVENTION

Antimonic acid or polyantimonic acid as used herein can be prepared by various procedures, such as hydrolysis of potassium antimonate $KSb(OH)_6$ using acids such as nitric acid or a cation exchange resin; hydrolysis of antimony pentachloride using bases such as aqueous ammonia; hydrolysis of a nitric acid oxidized antimony trichloride (i.e., the product of oxidation of antimony trichloride with nitric acid) using bases such as aqueous ammonia; oxidation of antimony trioxide with nitric acid in the presence of trivalent iron ions: and oxidation of antimony trioxide with hydrogen peroxide. A so-called antimony pentaoxide sol is also included in the scope of antimonic acid or polyantimonic acid. Both antimonic acid and polyantimonic acid can be represented by the general formula $Sb_2O_5 \cdot nH_2O$ (wherein n=1 to 6) as hydrates of the oxide of antimony (V).

Antimonic acid or polyantimonic acid salts are compounds resulting from substitution of a hydrogen ion or ions of the above antimonic acid or polyantimonic acid with other cations, such as ammonium, sodium, potassium, magnesium, copper, zinc, nickel, cobalt, iron, manganese, etc.

Antimony trioxide as used herein is an oxide of antimony (III). In general, commercially available antimony trioxide can be conveniently used. Such antimony trioxide is usually produced by a roasting of antimony trisulfide or oxidation of metal antimony with air. This is in the form of particles having a size of from about 0.1 to 10μ. The crystal form is either of the monoclinic system or of the rhombic system. Thus examples of the antimony trioxide as used herein include senarmontite (monoclinic system), valentinite (rhombic system), or a mixture thereof. Antimony trioxide can be prepared by various procedures such as hydrolysis of antimony trichloride using, for example, aqueous ammonia, sodium hydroxide, potassium hydroxide, and sodium carbonate, or oxidation of a metal antimony with air.

In the present invention, (A) at least one of antimonic acid, polyantimonic acid and the salts thereof, and (B) antimony trioxide are suspended in water and mixed.

The amount of antimony provided by the antimony trioxide used is from about 0.1 to 70 atomic %, preferably from 1 to 50 atomic %, and more preferably from 5 to 30 atomic % of the total amount of antimony present in an aqueous slurry just before drying.

Antimony trioxide reacts with antimonic acid relatively rapidly. The temperature range of less than about 150° C., specifically from room temperature (about 15° C.) to about 110° C., is preferred from the standpoints of operation efficiency and rate of reaction. Reaction occurs to be sufficient extent if it is performed within the above temperature range for from about 0.1 to 50 hours. As the temperature is increased, the reaction rate is increased. Where the antimonic acid, polyantimonic acid or salts thereof has a higher degree of crystallinity and the particle size of antimony trioxide is very large, the reaction rate is slow. Generally, the antimony trioxide is preferably used in the form of particles having a size of 10 microns or less, more preferably 5 microns or less.

The pH of the liquid can be varied over a wide range. That is, the reaction proceeds at a commercially acceptable rate over a wide pH range (i.e., preferably a pH of 12 or less, more preferably a pH of 10 or less) from an acid side to a weak alkaline side. The reaction rate tends to decrease to a certain extent as the pH is increased and made more alkaline.

The detailed mechanism of the reaction is not at present clear. While not desiring to be bound, it is observed, however, that all or part of the crystalline antimony trioxide added disappears and the particle size is decreased. The progress of the reaction can be monitored by analyses such as X-ray diffraction and electron microscopy. X-ray diffraction analysis shows that crystalline antimony trioxide disappears. Electron microscopy shows that the particle size of the antimony trioxide is reduced to several tens of microns.

It is believed that the occurrence of the above reaction advantageously influences the activity and physical properties of the ultimate catalyst. Furthermore, the reproducibility in preparation of the catalyst is increased.

Components other than the antimony component can be added in any suitable manner. It is essential for the process of the present invention that (A) at least one of antimonic acid, polyantimonic acid and the salts thereof and (B) antimony trioxide are mixed and reacted in an aqueous slurry state. If they are mixed in a dry state, the reaction hardly proceeds. That is, the object of the present invention cannot be attained by mixing them in a dry state.

In connection with the production of antimony-containing metal oxide catalysts, the methods described in Japanese Patent Publication Nos. 18722/72 and 18723/72 (corresponding to U.S. Pat. Nos. 3,657,155 and 3,686,138, respectively) are known as being capable of producing catalysts having good activity and physical properties.

Application of the process of the present invention to the above methods is especially effective and furthermore advantageous.

The former method, i.e., the method of U.S. Pat. No. 3,657,155 includes a step of oxidation of antimony trioxide using nitric acid in an aqueous slurry state in the presence of trivalent iron ions. In this oxidation step, at least part of the antimony trioxide is converted into $Sb_2O_5 \cdot nH_2O$ and $FeSbO_4$ (as a result of its reaction with trivalent iron ions which are also present) and simultaneously the generation of $N_2$ gas (along with small amounts of $NO_x$ gases) mainly due to the reductive decomposition of nitric acid occurs. The thus-formed gases produce bubbles in the aqueous slurry and these bubbles do not break within short periods of time, i.e., long periods of time elapse before the bubbles disappear due to the collapse thereof. In practice of this method, therefore, the problem of overflow of the reaction vessel by the slurry often occurs. When the process of the present invention is employed in the above method described in U.S. Pat. No. 3,657,155, the reaction rate can be increased and further the problem of overflow of the reaction vessel by the slurry can be overcome.

The latter method, i.e., the method of U.S. Pat. No. 3,686,138 involves use of a pentavalent antimony compound as the antimony component.

When the process of the present invention is applied to either of these methods, catalysts with even further enhanced activity and physical properties can be obtained with very high reproducibility. Furthermore, an economic advantage that the optimum calcination temperature is reduced (i.e., energy is saved) and an operational advantage that the density of the catalyst particles is somewhat reduced occur. Thus results in the ability to obtain good fluidization.

Various types of antimony-containing metal oxide catalysts can be produced. Preferred are those catalysts represented by the empirical formula as shown below.

$$Me_aSb_bX_cQ_dR_eO_f(SiO_2)_g$$

wherein:

Me = at least one element selected from the group consisting of Fe, Co, Ni, Sn, U, Cr, Cu, Mn, Ti, and Ce;

X = at least one element selected from the group consisting of V, Mo, and W;

Q = at least one element selected from the group consisting of Li, Na, K, Rb, Cs, Be, Mg, Ca, Sr, Ba, Y, La, Th, Zr, Hf, Nb, Ta, Cr, Re, Ru, Os, Rh, Ir, Pd, Pt, Ag, Zn, Cd, Al, Ga, In, Tl, Ge, Pb, As, and Se;

R = at least one element selected from the group consisting of B, P, Te, and Bi; and the subscripts a, b, c, d, e, f, and g denote atomic ratios and are as follows:

a = 5 to 15, preferably 7 to 13;
b = 5 to 100, preferably 10 to 50;
c = 0 to 15, preferably 0.05 to 5;
d = 0 to 50, preferably 0 to 10;
e = 0 to 10, preferably 0.1 to 10;
f = a number corresponding to the oxide formed when all the components are bound together; and
g = 10 to 200, preferably 20 to 200. These catalyst compositions may be used as such or, alternatively, may be deposited on suitable carriers such as silica, alumina, silica/alumina, silica/titania, titania, and zirconia. Of these carriers, silica is particularly preferred.

The catalyst can be used in both fixed-bed and fluidized-bed reaction zones. The catalyst can in particular be used as a fluidized-bed. In this case, it is preferred that in the above empirical formula g = 20 to 200.

Production of these catalysts are hereinafter explained in detail.

(i) An aqueous slurry containing (A) at least one of antimonic acid, polyantimonic acid and the salts thereof is prepared.

(ii) Antimony trioxide is added to the aqueous slurry in such an amount that the antimony provided by the antimony trioxide constitutes from about 0.1 to 70 atomic %, preferably from 1 to 50 atomic %, and more preferably from 5 to 30 atomic % of the total amount of antimony, and the resulting slurry mixture is maintained at a temperature of not more than about 150° C., preferably from room temperature (about 15° C.) to 110° C., for a period of from about 0.1 to 50 hours, preferably from 10 minutes to 2 hours.

(iii) A slurry containing as essential components the above antimony component, a compound of a polyvalent metal element, e.g., of an element such as iron, cobalt, nickel, tin, uranium, chromium, copper, manganese, titanium, vanadium, molybdenum, tungsten, tellurium, bismuth, arsenic, thorium, and cerium, and a silica sol is prepared.

(iv) The slurry prepared in (iii) above is then heated and dried to yield a solid substance.

(v) The solid substance is calcined at a temperature of from 200° to 950° C.

This calcination may be performed at a constant temperature, or may be a two step procedure, i.e., a preliminary calcination and a high temperature calcination. If it is desired for the solid substance to be calcined at temperatures as high as at least about 700° C., it is preferred that the calcination process be performed into two steps, a preliminary calcination and a high temperature calcination. In this case, the preliminary calcination is preferably carried out within the temperature range of from about 200° to 600° C. The optimum calcination conditions vary depending on the catalyst composition. In general, it is preferred for the solid substance to be preliminarily calcined at a temperature of from about 200° to 600° C. for a period of from about 1 to 50 hours and then at an elevated temperature of from about 600° to 950° C. for a period of from about 1 to 50 hours. In one step calcination procedure, it is preferred for the solid substance to be calcined at a temperature of from about 500° to 900° C. for a period of from about 1 to 50 hours.

In the process of the present invention, the order in which the antimony component, polyvalent metal compound, and silica sol are mixed is not critical and can be determined appropriately. Antimony trioxide may be added to a mixed slurry of the antimonic acid, the polyvalent metal compound, and the silica sol. In cases where the other components are added, the order of adding the components is not critical and any addition order can be used.

In preparing a fluidized-bed catalyst, it is particularly preferred to employ a method in which the pH of the mixed slurry is adjusted to a pH of 7 or less, preferably a pH of 4 or less, heated at a temperature of from about 40° to 150° C. for a period of from about 5 minutes to 10 hours, and then spray dried. For calcination of the solid substance, it is preferred to employ a fluidized-bed calcination method.

When, on the other hand, a fixed-bed catalyst is prepared, the mixed slurry can be dried, the thus-formed solid substance is heated at a temperature of at least about 200° C. to decompose and remove volatile components such as ammonium nitrate and, thereafter, it is molded and, if necessary, calcined.

The sources of the starting materials for use in the preparation of the above catalyst can be those conventionally use, e.g., as described in U.S. Pat. Nos. 3,657,155, 3,716,496, 4,083,804, etc.

Antimony-containing metal oxide catalysts prepared by the process of the present invention are useful for production of aldehydes and acids through oxidation of organic compounds, for production of nitriles through ammoxidation of organic compounds, and for production of dienes, unsaturated aldehydes, and unsaturated acids through oxidative dehydrogenation of organic compounds such as paraffins, olefins, alkyl aromatics, alkyl heterocyclic compounds, alcohols, aldehydes, etc.

The present invention is described in greater detail by reference to the following Examples and Comparative Examples which are not to be construed as limiting the scope of this invention.

The yield of the desired product for the Examples and Comparative Examples is defined herein as follows:

Yield (%) =

$$\frac{\text{Weight of Carbon in Desired Product Formed (g)}}{\text{Weight of Carbon in Organic Compound Starting Materials Supplied (g)}} \times 100$$

The activity of the catalysts in the Examples and Comparative Examples herein was tested in connection with ammoxidation of propylene.

Test Condition (1)

A U-shaped steel tube with an inner diameter of 16 mm was charged with 50 ml of catalyst molded in a cylindrical form, measuring 2 mm in length and 2 mm in diameter. This tube was placed in a fluidized-bed bath and heated.

A gas mixture having the composition as shown below was introduced into the tube at a rate of 10 liters per hour (NTP), and the reaction was performed at atmospheric pressure.

$O_2$ (supplied as air):propylene=2.2:1 (molar basis)
$NH_3$:propylene=1.3:1 (molar basis)

Test Condition (2)

The catalyst was placed in a catalyst section (inner diameter: 2.3 cm and height: 40 cm) of a fluidized-bed reactor, and a gas mixture having the composition as shown below was introduced thereinto. The reaction was performed at atmospheric pressure.

$O_2$ (supplied as air):propylene=2.2:1 (molar basis)
$NH_3$:propylene=1.1:1 (molar basis)

EXAMPLE 1

A catalyst having the empirical formula: $Fe_{10}Sb_{25}W_{0.25}O_{65.8}(SiO_2)_{30}$ was prepared as follows.

54.9 g of powdered metal antimony was added in small portions to 230 ml of nitric acid heated at 80° C. (specific gravity: 1.38). After all of the antimony was added and the evolution of brown gas stopped, the mixture was allowed to stand at room temperature for 16 hours. Then excess nitric acid was removed, and the precipitate formed was washed three times with 100 ml of water. (I)

11.2 g of powdered electrolytic iron was added in small portions to and completely dissolved in a mixture of 81 ml of nitric acid (specific gravity: 1.38) and 100 ml of water at 80° C. (II)

1.3 g of ammonium paratungstate was dissolved in 50 ml of water. (III)

180 g of silica sol ($SiO_2$, 20% by weight) was weighed out. (IV)

The above-prepared ingredients (I) to (IV) were thoroughly mixed and the pH of the mixture was adjusted to 2 by adding aqueous ammonia (28% by weight) in small portions while stirring. They were reacted at reflux at 100° C. for 5 hours.

Thus, most of the antimony was converted into a pentavalent form and an antimonic acid/iron antimonate mixture was formed.

To this slurry was added 7.3 g of antimony trioxide, and the resulting mixture was allowed to stand at room temperature for 30 minutes while stirring. Part of the slurry was removed and subjected to an X-ray diffraction analysis. This X-ray diffraction analysis showed that crystalline antimony trioxide disappeared.

The mixture was dried, and calcined at 200° C. for 2 hours and then at 400° C. for 2 hours. Then water was added, and the resulting mixture was kneaded and molded into a cylindrical form measuring 2 mm in length and 2 mm in diameter. These molds were dried at 130° C. for 16 hours and then calcined at 800° C. for 3 hours

EXAMPLE 2

A catalyst having the empirical formula: $Fe_{10}Sb_{25}W_{0.25}O_{65.8}(SiO_2)_{30}$ was prepared in the same manner as described in Example 1 except that the amount of antimony trioxide added to the slurry was reduced to 1/5 of that of Example 1.

EXAMPLE 3

A catalyst having the empirical formula: $Fe_{10}Sb_{25}W_{0.25}O_{65.8}(SiO_2)_{30}$ was prepared in the same manner as in Example 1 except that the amount of antimony trioxide added to the slurry was reduced to ½ of that of Example 2.

COMPARATIVE EXAMPLE 1

A catalyst having the same empirical formula as described in Example 1 was prepared as follows.

61 g of powdered metal antimony was added in small portions to 230 ml of nitric acid heated at 80° C. (specific gravity: 1.38). After all of the antimony was added and the evolution of brown gas stopped, the mixture was allowed to stand at room temperature for 16 hours. Then, excess nitric acid was removed, and the precipitate formed was washed three times with 100 ml of water. (I)

11.2 g of powdered electrolytic iron was added in small portions to a mixture of 81 ml of nitric acid (specific gravity: 1.38) and 100 ml of water at 80° C. and completely dissolved therein. (II)

1.3 g of ammonium paratungstate was dissolved in 50 ml of water. (III)

180 g of silica sol ($SiO_2$, 20% by weight) was weighed out. (IV)

The above-prepared ingredients (I) to (IV) were throughly mixed and the pH of the mixture was adjusted to 2 by adding aqueous ammonia (28% by weight) in small portions while stirring. They were reacted at reflux at 100° C. for 5 hours.

The reaction mixture was dried, and calcined at 200° C. for 2 hours and then at 400° C. for 2 hours. Then, water was added, and the resulting mixture was kneaded and molded into a cylindrical form, measuring 2 mm in length and 2 mm in diameter. These molds were dried at 130° C. for 16 hours, and then calcined at 800° C. for 3 hours.

COMPARATIVE EXAMPLE 2

A catalyst having the same empirical formula as described in Example 1 was prepared as follows.

54.9 g of powdered metal antimony was added in small portions to 230 ml of nitric acid heated at 80° C. (specific gravity, 1.38). After all of the antimony was added and the evolution of brown gas stopped, the mixture was allowed to stand at room temperature for 16 hours. Then, excess nitric acid was removed, and the precipitate formed was washed three times with 100 ml of water. (I)

11.2 g of powdered electrolytic iron was added in small portions to a mixture of 81 ml of nitric acid (specific gravity: 1.38) and 100 ml of water at 80° C. and dissolved therein completely. (II)

1.3 g of ammonium paratungstate was dissolved in 50 ml of water. (III)

180 g of silica sol ($SiO_2$, 20% by weight) was weighed out. (IV)

The above-prepared ingredients (I) to (IV) were thoroughly mixed and the pH of the mixture was adjusted to 2 by adding aqueous ammonia (28% by weight) in small portions while stirring. The resulting mixture was reacted under reflux at 100° C. for 5 hours.

The reaction mixture was dried, and calcined at 200° C. for 2 hours and then at 400° C. for 2 hours. Then, 7.3 g of antimony trioxide and water were added, and the resulting mixture was kneaded and molded into a cylindrical form, measuring 2 mm in length and 2 mm in diameter. These molds were dried at 130° C. for 16 hours and then calcined at 800° C. for 2 hours.

EXAMPLE 4

A catalyst having the empirical formula: $Sn_{10}Sb_{60}O_{140}(SiO_2)_{30}$ was prepared as follows.

1,550 g of an antimonic acid slurry ($Sb_2O_5$, 10% by weight) and 30.1 g of powdered tin dioxide were mixed and maintained at 100° C. at reflux for 2 hours. 35 g of antimony trioxide was added thereto, and the resulting mixture was maintained at the same temperature as above for 20 minutes.

X-ray diffraction analysis of the slurry showed that crystalline antimony trioxide disappeared.

To this slurry was added 180 g of silica sol ($SiO_2$, 20% by weight), and the mixture was evaporated to dryness while fully stirring. The thus-formed solid mass was calcined at 200° C. for 2 hours and then at 400° C. for 2 hours. Water was then added, and the resulting mixture was kneaded and molded into a cylindrical form measuring 2 mm in length and 2 mm in diameter. These molds were dried at 130° C. for 16 hours and then calcined at 820° C. for 2 hours.

COMPARATIVE EXAMPLE 3

A catalyst having the same empirical formula as described in Example 4 was prepared in the same manner as described in Example 4 except that all of the antimony component was added as an antimonic acid slurry; and antimony trioxide was not used.

EXAMPLE 5

A catalyst having the empirical formula: $U_{10}Sb_{50}W_{0.1}Te_{0.5}O_{128}(SiO_2)_{60}$ was prepared as follows.

1,130 g of an antimonic acid slurry ($Sb_2O_5$, 10% by weight) was weighed out. (I)

100 g of uranyl nitrate was dissolved in 100 g of water. (II)

0.52 g of ammonium paratangstate was dissolved in 30 ml of water. (III)

1.3 g of powdered metal tellurium was dissolved in 60 g of nitric acid (specific gravity: 1.38). (IV)

361 g of silica sol ($SiO_2$, 20% by weight) was weighed out. (V)

The above-prepared ingredients (I) to (V) were mixed and refluxed at 100° C. for 2 hours.

To the thus-formed slurry was added 43.7 g of antimony trioxide, and the resulting mixture was stirred for 30 minutes.

The mixture was evaporated to dryness, and calcined at 200° C. for 2 and then at 400° C. for 2 hours. Water was then added, and the resulting mixture was kneaded and molded into a cylindrical form measuring 2 mm in length and 2 mm in diameter. These molds were dried at 130° C. for 16 hours and then calcined at 810° C. for 5 hours.

COMPARATIVE EXAMPLE 4

A catalyst having the same empirical formula as described in Example 5 was prepared in the same manner as in described in Example 5 except that all of the antimony component was added as an antimonic acid slurry; and antimony trioxide was not used.

EXAMPLE 6

A catalyst having the empirical formula: $Fe_{10}Sb_{25}W_{0.25}Te_{1.0}O_{67.8}(SiO_2)_{30}$ was prepared as follows.

0.98 kg of powdered metal antimony was weighed out. 7.2 l of nitric acid (specific gravity: 1.38) was heated to about 80° C., and the powdered metal antimony was gradually added thereto. After complete oxidation of the antimony was confirmed, excess nitric acid was removed. The antimony oxide thus prepared using nitric acid was washed five times with 2 l of water and, thereafter, was placed in a ball mill and pulverized for 3 hours. (I)

0.358 kg of powdered electrolytic iron was weighed out. 3 l of nitric acid (specific gravity: 1.38) was mixed with 4 l of water, and the resulting mixture was heated to about 80° C. The powdered electrolytic iron was gradually added and completely dissolved therein. (II)

41.8 g of ammonium paratungstate was dissolved in 2 l of water. (III)

147 g of telluric acid was dissolved in 1 l or water. (IV)

5.76 kg of silica sol ($SiO_2$, 20% by weight) was weighed out. (V)

The above-prepared ingredients (I) to (V) were mixed and the pH of the mixture was adjusted to 2 by gradually adding aqueous ammonia (15% by weight) with good stirring.

The thus-prepared slurry was heated at 100° C. for 4 hours. After the slurry was cooled, 1,168 g of antimony trioxide was added thereto, and the resulting mixture was stirred for 30 minutes.

The mixture was then spray dried in the usual manner using a spray drying apparatus. The thus-produced fine spherical particles were calcined at 200° C. for 4 hours, at 400° C. for 4 hours, and further at 800° C. for 8 hours in a stream of air in a fluidized-bed calcination furnace.

COMPARATIVE EXAMPLE 5

A catalyst having the same empirical formula as described in Example 6 was prepared in the same manner as described in Example 6 except that all of the antimony component was added at the same time as the metal antimony and the final calcination was performed at 800° C. for 8 hours.

EXAMPLE 7

A catalyst having the empirical formula: $Fe_{10}Cu_3Sb_{23}Mo_1Te_2O_{71}(SiO_2)_{55}$ was prepared in the same manner as described in Example 6 except that copper nitrate was used as the Cu starting material, ammonium paramolybdate was used as the Mo starting material, and powdered metal tellurium dissolved in nitric acid was used as the Te starting material, 5 atomic % of the total amount of the antimony was the antimony provided by the antimony trioxide, and that the final calcination was performed at 745° C. for 4 hours.

EXAMPLE 8

A catalyst having the empirical formula: $Fe_{10}Cu_{3.5}Sb_{23}Mo_{0.5}W_{0.2}Zn_{0.5}B_{0.5}P_{0.1}Te_{1.3}O_{70.7}(SiO_2)_{55}$ was prepared in the same manner as described in Example 6 except that:

copper nitrate was used as the Cu starting material: ammonium paramolybdate, as the Mo starting material; ammonium paratungstate, as the W starting material; zinc nitrate, as the Zn starting material; orthoboric acid, as the B starting material; orthophosphoric acid, as the P starting material; and telluric acid, as the Te starting material;

10 atomic % of the total amount of the antimony was the antimony provided by the antimony trioxide; and the final calcination was performed at 775° C. for 4 hours.

COMPARATIVE EXAMPLE 6

A catalyst having the same empirical formula as described in Example 8 was prepared in the same manner as described in Example 6 except that all of the antimony component was added at the same time as the metal antimony, and that the final calcination was performed at 775° C. for 4 hours.

The bulk density of the catalyst was 1.16 g/ml while on the other hand that of the catalyst of Example 8 was 1.05 g/ml. That is, the bulk density of the catalyst of this Comparative Example was about 10% greater than that of the catalyst of Example 8. Thus the fluidization characteristics of the catalyst were disadvantageous when used in a fluidized-bed reaction.

EXAMPLE 9

A catalyst having the empirical formula: $Fe_{10}U_3Sb_{2.5}Mo_{0.5}Te_{1.0}O_{76.5}(SiO_2)_{55}$ was prepared in the same manner as described in Example 6 except that:

uranyl nitrate was used as the U starting material; ammonium paramolybdate, as the Mo starting material; and telluric acid, as the Te starting material;

15 atomic % of the total amount of the antimony was the antimony provided by the antimony trioxide; and the final calcination was performed at 800° C. for 5 hours.

EXAMPLE 10

A catalyst having the empirical formula: $Fe_{10}Ni_{0.5}Sn_{0.5}Sb_{20}Ti_{0.5}Mo_{0.7}V_{0.1}Te_{1.5}O_{62.9}(SiO_2)_{60}$ was prepared in the same manner as in Example 6 except that:

nickel nitrate was used as the Ni starting material; powdered metal tin oxidized with nitric acid, as the Sn starting material; powdered titanium dioxide, as the Ti starting material; ammonium paramolybdate, as the Mo starting material; ammonium metavanadate, as the V starting material; and powdered metal tellurium oxidized with nitric acid, as the Te starting material;

10 atomic % of the total amount of the antimony was the antimony provided by the antimony trioxide; and the final calcination was performed at 790° C. for 4 hours.

COMPARATIVE EXAMPLE 7

A catalyst having the same empirical formula as described in Example 10 was prepared in the same manner as described in Example 6 except that all of the antimony component was added at the same time as metal antimony.

The catalysts of the above Examples and Comparative Examples were subjected to activity testing under the activity Test Condition(1)or(2). The results obtained are shown in the Table below.

TABLE 1

| Run No. | Catalyst Empirical formula (atomic ratio) | (Sb in Antimony Trioxide/Total Sb) × 100 (atomic %) | Activity Test Condition | Reaction Temperature (°C.) | Yield of Acrylonitrile (%) | Conversion of Propylene (%) |
|---|---|---|---|---|---|---|
| Example 1 | $Fe_{10}Sb_{25}W_{0.25}O_{65.8}(SiO_2)_{30}$ | 10 | (1) | 450 | 73 | 99 |
| Example 2 | $Fe_{10}Sb_{25}W_{0.25}O_{65.8}(SiO_2)_{30}$ | 2 | (1) | 450 | 70 | 100 |
| Example 3 | $Fe_{10}Sb_{25}W_{0.25}O_{65.8}(SiO_2)_{30}$ | 5 | (1) | 450 | 73 | 99 |
| Comparative Example 1 | $Fe_{10}Sb_{25}W_{0.25}O_{65.8}(SiO_2)_{30}$ | — | (1) | 450 | 68 | 100 |
| Comparative Example 2 | $Fe_{10}Sb_{25}W_{0.25}O_{65.8}(SiO_2)_{30}$ | 10 (mixed in dry state) | (1) | 450 | 69 | 100 |
| Example 4 | $Sn_{10}Sb_{60}O_{140}(SiO_2)_{30}$ | 20 | (1) | 460 | 65 | 95 |
| Comparative Example 3 | $Sn_{10}Sb_{60}O_{140}(SiO_2)_{30}$ | — | (1) | 460 | 63 | 97 |
| Example 5 | $U_{10}Sb_{50}W_{0.1}Te_{0.5}O_{128}(SiO_2)_{60}$ | 30 | (1) | 480 | 75 | 96 |
| Comparative Example 4 | $U_{10}Sb_{50}W_{0.1}Te_{0.5}O_{128}(SiO_2)_{60}$ | — | (1) | 480 | 72 | 100 |
| Example 6 | $Fe_{10}Sb_{25}W_{0.25}Te_{1.0}O_{67.8}(SiO_2)_{30}$ | 47.3 | (2) | 460 | 79 | 98 |
| Comparative Example 5 | $Fe_{10}Sb_{25}W_{0.25}Te_{1.0}O_{67.8}(SiO_2)_{30}$ | — | (2) | 460 | 77 | 100 |
| Example 7 | $Fe_{10}Cu_3Sb_{23}Mo_1Te_2O_{71}(SiO_2)_{55}$ | 5 | (2) | 440 | 83 | 97 |
| Example 8 | $Fe_{10}Cu_{3.5}Sb_{23}Mo_{0.5}W_{0.2}Zn_{0.5}B_{0.5}P_{0.1}Te_{1.3}O_{70.7}(SiO_2)_{55}$ | 10 | (2) | 450 | 85 | 98 |
| Example 9 | $Fe_{10}U_3Sb_{25}Mo_{0.5}Te_{1.0}O_{76.5}(SiO_2)_{50}$ | 15 | (2) | 450 | 83 | 98 |
| Example 10 | $Fe_{10}Ni_{0.5}Sn_{0.5}Sb_{20}Ti_{0.5}Mo_{0.7}V_{0.1}Te_{1.5}O_{62.9}(SiO_2)_{60}$ | 10 | (2) | 440 | 83 | 99 |
| Comparative Example 6 | Same as in Example 8 | — | (2) | 450 | 82 | 99 |
| Comparative Example 7 | Same as in Example 10 | — | (2) | 450 | 82 | 100 |

From the results in the table above, it is clear that the catalysts produced according to the process of the pres-

What is claimed is:

1. A process for producing an antimony-containing metal oxide catalyst, wherein the antimony-containing metal oxide catalyst has the following empirical formula:

$$Me_aSb_bX_cQ_dR_eO_f(SiO_2)_g$$

wherein:
Me = at least one element selected from the group consisting of Fe, Co, Ni, Sn, U, Cr, Cu, Mn, Ti and Ce;
X = at least one element selected from the group consisting of V, Mo and W;
Q = at least one element selected from the group consisting of Li, Na, K, Rb, Cs, Be, Mg, Ca, Sr, Ba, Y, La, Zr, Th, Hf, Nb, Ta, Cr, Re, Ru, Os, Rh, Ir, Pd, Pt, Ag, Zn, Cd, Al, Ga, In, Tl, Ge, Pb, As and Se;
R = at least one element selected from the group consisting of B, P, Te and Bi; and
the subscripts a, b, c, d, e, f and g denote atomic ratios and are as follows:
a = 5 to 15;
b = 5 to 100;
c = 0 to 15;
d = 0 to 50;
e = 0 to 10;
f = a number corresponding to the oxide formed when all the components are bound together; and
g = 10 to 200, which process comprises
(1) preparing an aqueous slurry containing as essential componets an antimony component, one or more polyvalent metal compounds, and silica sol,
(2) heating and drying the slurry to form a solid product, and
(3) then calcining the solid product, wherein as the antimony component of step (1) a mixture of
(A) at least one of antimonic acid, polyantimonic acid and the salts thereof and
(B) antimony trioxide is used, the process comprises mixing (A) and (B) in such a manner that the antimony provided by the antimony trioxide constitutes from 0.1 to 70 atomic % of the total amount of antimony and further in an aqueous slurry state.

2. The process as claimed in claim 1, wherein the aqueous slurry containing (A) at least one of antimonic acid, polyantimonic acid and the salts thereof, and (B) antimony trioxide is maintained at a temperature of about 150° C. or less for a period of from about 0.1 to 50 hours prior to heating and drying in step (2).

3. The process as claimed in claim 2, wherein the calcining of the solid product is at from about 500° to 950° C.

4. The process as claimed in claim 3, wherein the polyvalent metal compound is a compound of at least one metal selected from the group consisting of iron, cobalt, nickel, tin, uranium, chromium, copper, manganese, titanium, vanadium, molybdenum, tungsten, tellurium, bismuth, arsenic, thorium, and cerium.

5. The process as claimed in claim 4, wherein the antimonic acid or polyantimonic acid is prepared by any one of the following methods:
(i) hydrolysis of an antimonic acid salt with an acid;
(ii) hydrolysis of antimony pentachloride with a base;
(iii) hydrolysis of a nitric acid oxidized antimony trihalide with a bases;
(iv) oxidation of antimony trioxide with nitric acid in the presence of trivalent iron ion; and
(v) oxidation of antimony trioxide with hydrogen peroxide.

6. The process as claimed in claim 3, wherein the antimonic acid or polyantimonic acid is prepared by any one of the following methods:
(i) hydrolysis of an antimonic acid salt with an acid;
(ii) hydrolysis of antimony pentachloride with a base;
(iii) hydrolysis of a nitric acid oxidized antimony trihalide with a bases;
(iv) oxidation of antimony trioxide with nitric acid in the presence of trivalent iron ion; and
(v) oxidation of antimony trioxide with hydrogen peroxide.

7. The process as claimed in claim 2, wherein the polyvalent metal compound is a compound of at least one metal selected from the group consisting of iron, cobalt, nickel, tin, uranium, chromium, copper, manganese, titanium, vanadium, molybdenum, tungsten, tellurium, bismuth, arsenic, thorium, and cerium.

8. The process as claimed in claim 7, wherein the antimonic acid or polyantimonic acid is prepared by any one of the following methods:
(i) hydrolysis of an antimonic acid salt with an acid;
(ii) hydrolysis of antimony pentachloride with a base;
(iii) hydrolysis of a nitric acid oxidized antimony trihalide with a bases;
(iv) oxidation of antimony trioxide with nitric acid in the presence of trivalent iron ion; and
(v) oxidation of antimony trioxide with hydrogen peroxide.

9. The process as claimed in claim 2, wherein the antimonic acid or polyantimonic aicd is prepared by any one of the following methods:
(i) hydrolysis of an antimonic acid salt with an acid;
(ii) hydrolysis of antimony pentachloride with a base;
(iii) hydrolysis of a nitric acid oxidized antimony trihalide with a bases;
(iv) oxidation of antimony trioxide with nitric acid in the presence of trivalent iron ion; and
(v) oxidation of antimony trioxide with hydrogen peroxide.

10. The process as claimed in claim 2, wherein the process comprises heating and drying by spray drying in step (2) and calcining in step (3) to yield the solid catalyst particles.

11. The process as claimed in claim 10, wherein the calcining of the said product is by calcining in a fluidized-bed calcination furnace such that the particles are fluidized, thereby producing a fluidized-bed catalyst.

12. The process as claimed in claim 1 wherein the calcining of the solid product is at from about 500° to 950° C.

13. The process as claimed in claim 12, wherein the polyvalent metal compound is a compound of at least one metal selected from the group consisting of iron, cobalt, nickel, tin, uranium, chromium, copper, manganese, titanium, vanadium, molybdenum, tungsten, tellurium, bismuth, arsenic, thorium, and cerium.

14. The process as claimed in claim 13, wherein the antimonic acid or polyantimonic acid is prepared by any one of the following methods:
 (i) hydrolysis of an antimonic acid salt with an acid;
 (ii) hydrolysis of antimony pentachloride with a base;
 (iii) hydrolysis of a nitric acid oxidized antimony trihalide with a bases;
 (iv) oxidation of antimony trioxide with nitric acid in the presence of trivalent iron ion; and
 (v) oxidation of antimony trioxide with hydrogen peroxide.

15. The process as claimed in claim 12, wherein the antimonic acid or polyantimonic acid is prepared by any one of the following methods:
 (i) hydrolysis of an antimonic acid salt with an acid;
 (ii) hydrolysis of antimony pentachloride with a base;
 (iii) hydrolysis of a nitric acid oxidized antimony trihalide with a bases;
 (iv) oxidation of antimony trioxide with nitric acid in the presence of trivalent iron ion; and
 (v) oxidation of antimony trioxide with hydrogen peroxide.

16. The process as claimed in claim 1, wherein the polyvalent metal compound is a compound of at least one metal selected from the group consisting of iron, cobalt, nickel, tin, uranium, chromium, copper, manganese, titanium, vanadium, molybdenum, tungsten, tellurium, bismuth, arsenic, thorium, and cerium.

17. The process as claimed in claim 16, wherein the antimonic acid or polyantimonic acid is prepared by any one of the following methods:
 (i) hydrolysis of an antimonic acid salt with an acid;
 (ii) hydrolysis of antimony pentachloride with a base;
 (iii) hydrolysis of a nitric acid oxidized antimony trihalide with a bases;
 (iv) oxidation of antimony trioxide with nitric acid in the presence of trivalent iron ion; and
 (v) oxidation of antimony trioxide with hydrogen peroxide.

18. The process as claimed in claim 1, wherein the antimonic acid or polyantimonic acid is prepared by any one of the following methods:
 (i) hydrolysis of an antimonic acid salt with an acid;
 (ii) hydrolysis of antimony pentachloride with a base;
 (iii) hydrolysis of a nitric acid oxidized antimony trihalide with a bases;
 (iv) oxidation of antimony trioxide with nitric acid in the presence of trivalent iron ion; and
 (v) oxidation of antimony trioxide with hydrogen peroxide.

19. The process as claimed in claim 1, wherein the silica sol is an aqueous sol containing from 5 to 90% by weight of silica.

20. The process as claimed in claim 1, wherein the process comprises heating and drying by spray drying in step (2) and calcining in step (3) to yield the solid catalyst particles.

21. The process as claimed in claim 20, wherein the calcining of the said product is by calcining in a fluidized-bed calcination furnace such that the particles are fluidized, thereby producing a fluidized-bed catalyst.

22. The process as claimed in claim 1, wherein the process comprises heating and drying by spray drying in step (2) and calcining in step (3) to yield the solid catalyst particles.

23. The process as claimed in claim 22, wherein the calcining of the said product is by calcining in a fluidized-bed calcination furnace such that the particles are fluidized, thereby producing a fluidized-bed catalyst.

* * * * *